United States Patent [19]
Vicki et al.

[11] Patent Number: 4,610,157
[45] Date of Patent: Sep. 9, 1986

[54] SURFACE PENETRANT INSPECTION TEST PIECE HAVING VARYING THICKNESS PLATING

[75] Inventors: Frank J. Vicki, Plantsville, Conn.; Setsuo Shimizu, Yokohama, Japan

[73] Assignee: United Technologies Corporation, Hartford, Conn.

[21] Appl. No.: 680,437

[22] Filed: Dec. 11, 1984

[51] Int. Cl.[4] ............................................. G01N 19/08
[52] U.S. Cl. ...................................... 73/1 R; 73/104; 73/799
[58] Field of Search .......................... 73/104, 799, 1 R

[56] References Cited

U.S. PATENT DOCUMENTS

| | | | |
|---|---|---|---|
| 3,164,006 | 1/1965 | Alburger | 73/104 X |
| 3,927,551 | 12/1975 | Alburger | 73/1 R |
| 3,946,597 | 3/1976 | Tahbaz | 73/104 X |
| 4,078,417 | 3/1978 | Shigekawa | 73/1 R |

FOREIGN PATENT DOCUMENTS

| | | |
|---|---|---|
| 14633 | 4/1974 | Japan . |
| 23161 | 9/1981 | Japan . |
| 32145 | 10/1981 | Japan . |

OTHER PUBLICATIONS 1965 (Proposed) U.S. Military Specification Mil-I-8963 (ASG) Inspection Materials, Fluorescent Penetrant pp. 1-3, 18-24.

*Primary Examiner*—Stewart J. Levy
*Assistant Examiner*—Joseph W. Roskos
*Attorney, Agent, or Firm*—C. G. Nessler

[57] ABSTRACT

A test specimen has a carefully controlled series of cracks on its surface and is useful for evaluating surface penetrants employed in non-destructive inspection. A flat brass substrate has a nickel electroplating on one surface, which plating varies in thickness along the length of the panel. The opposing side of the panel has a multiplicity of grooves which locally concentrate strain in the plating when the panel is bent during manufacture, thus providing a crack associated with each groove. In a preferred embodiment, the texture of the cracked surface varies across the panel in the same direction in which the cracks run, thus enabling evaluation of the usefulness of penetrants in finding different size cracks under different surface finish conditions.

8 Claims, 4 Drawing Figures

SURFACE PENETRANT INSPECTION TEST PIECE HAVING VARYING THICKNESS PLATING

TECHNICAL FIELD

The present invention relates to test panels used for evaluating methods for finding cracks in workpieces, most particularly to the evaluation of surface penetrants.

BACKGROUND

For a number of years penetrants, such as dye penetrants and fluorescent penetrants, have been used for finding cracks and other flaws in the surfaces of workpieces. Generally, a penetrant material is infiltrated into the cracks of a workpiece and after the bulk of the material is wiped away, the residual material which is remaining in the crack is sought out optically. Various means, such as dyes, powders and fluorescing mediums are used to enhance the visibility of these penetrants. There are, of course, a considerable number of currently used commercially available penetrants and over the years even many more have been experimented with or offered to the public for sale. And even within the context of a supposedly constant and known penetrant, there may be variations in the extent to which the penetrant will reveal cracks. Such variations can result when the penetrant composition inadvertently changes, or the method of application changes over time.

In many applications it is of the most vital importance that the cracks beyond a certain size be found. Therefore, there has been a continuing need for a standard test method for evaluating a penetrant, and in particular to evaluating the sensitivity of a penetrant in finding particular cracks. Substantial effort in this direction is indicated by the 1965 U.S. Military Specification MIL-I-8963 (ASG) which was never officially issued. The specificiation discloses test panels made by a combination of nickel and chromium plating of brass panels. The panels are bent in curved dies to crack them at the plated surface. The crack type (size) varies according to the plating bath composition and operating parameters which are used.

The military specification reflects an ongoing endeavor to provide a standard test specimen with a standard crack pattern. Others have made specimens by mechanically or thermally fatigue cracking a substrate piece of material. However, the cracks in such specimens are generally too large and tend to be too variable from one specimen to the next. Further, there has always been a problem in removing the penetrant from the bottom of certain types of cracks, especially the foregoing, after a penetrant has been assessed. If residue from the penetrant accumulates in the crack, the crack is thereby made shallower and this change in character alters reproducibility in use of the test specimen.

A significant advance in making test specimen is revealed in Japanese patent publication No. 14633/1974 "Comparative Test. Specimen for Penetrant Test", by S. Shimizu, one of the applicants herein. Described in the Shimizu invention, a test specimen consists of a flat brass plate with one surface having a very precise thickness nickel plating and very thin chromium overcoat. Stress is imposed from the rear to crack the plating and to form a multiplicity of cracks running perpendicular to the length which is bent. The crack sizes correspond with the thickness of the nickel plated layer which varied controllably in different specimens from 2–50 micrometers, at least.

The foregoing panels have worked well but it is necessary to successively use panels with different plating thicknesses to determine the sensitivity of a particular penetrant. It has been recognized that improvements could be achieved if a range of crack sizes could be controllably provided on a single panel. Specifically, an improved panel will have a plating which varies gradually in thickness along its length. Such a panel is called herein a "tapered test panel" and is disclosed in Japanese patent applications No. 32145/1980 and No. 23161/1980, both of Y. Natori. The first patent discloses simply a tapered test panel without indicating the manner in which it might be plated or cracked. One can assume that it would be made in the same manner as described in the Shimizu patent. (According to Shimizu, plates are cracked by bending them in any arbitrary way, such as by pressing the plate over a rod laid transverse to its length.) The second patent of Natori discloses how a tapered thickness plating is detained on a test panel: The substrate is placed in a plating bath and there is a movable screen between the substrate and the cathode, which screen is raised or lowered across the front of the substrate to alter the current distribution and thereby the plating thickness.

While tapered test panels are thus revealed, in fact, they have not been able to be cracked easily in a manner which produces uniformly spaced cracks. That is, in the practice of Shimizu or the Military Specification with the uniform thickness platings, the bending moment which was applied to the panel, such as by simply stressing it over a pivot, was not so critical. No matter where the sufficient tensile stress is created in the nickel plating at the surface, any cracks would have depths which correspond with the thickness of the plating, which thickness is constant across the panel. But, in a tapered panel cracks must be uniformly present in one panel to the next. The reason is that when such panels are used, the distance from a reference end to the point where the crack penetrant visibility demarcates is measured. The demarcation point is gaged subjectively or objectively according to the intensity of fluorescence, color, etc. It is obvious that for accurate measurement there must be a certain minimum pitch of cracks. But less obviously, the quantity of cracking at any location influences the perception of the demarcation point. As an illustration, if at a given local region along the length of a first panel there is but single crack, but in a second similar panel there are a multiplicity of closely spaced cracks, then the intensity of signal will be greater in the second panel. If the second panel is mistakenly judged to indicate the penetrant finds a certain size crack whereas the first does not, such panels will have failed in their intended purpose of being standards.

In fact, all the conventional means of bending have been tried on tapered test panels but there has been variation in the placement and density of cracks. Such variation can be attributed both to bending techniques of insufficient precision and to the tapered panel being a somewhat complex varying shape structure. Because cracking has been non-uniform, tapered test panels have not been acceptable as standards.

DISCLOSURE OF THE INVENTION

An object of the invention is to provide in a multiplicity of taper test specimens a uniform spacing and density of cracks, so that such specimens may be used as surface penetrant standards.

According to the invention, a specimen having a tapered thickness plating on one side is physically modified on the opposite side to concentrate any imposed bending strain in local areas of the plating. Thus, when a specimen is suitably stressed, cracking will occur only at the predetermined locations associated with the stress concentrators. In the best mode of the invention a 2 mm thick flat brass panel is provided with a series of minute uniformly spaced grooves on the side of the panel opposite that which has a tapered thickness electroplating of nickel. The grooves are narrow, of about 0.2–0.5 mm width and they extend about 70–80% of the way through the substrate plate. The panel is then bent sufficiently to cause tensile crack failure of the plating and it is restraightened for use.

Since conventional machining can be used to readily make reproducible substrates and since the bending technique now becomes relatively non-critical, specimens with reproducible cracks can thus be made in a convenient and cost effective way.

In another embodiment of the invention, the surface finish of the plated surface is varied across its width. Surface finish roughness affects the perceived crack pattern of a penetrant because it affects the general retention of penetrant on the article surface. Thus, different specimens can be provided with different surface finishes. But, in a preferred embodiment, the surface finish of a specimen will vary across the surface in the direction transverse to the specimen length while the crack sizes vary in the direction parallel to the length. Thus each size crack will run from a rough to a smooth region and reveal the sensitivity of a penetrant in finding cracks under different surface finish conditions, according to the specific locations on the surface where transverse cracks are revealed.

The foregoing and other objects, features and advantages of the present invention will become more apparent from the following description of preferred embodiments and accompanying drawings.

BEST MODE FOR CARRYING OUT THE INVENTION

The invention is described in terms of a test specimen made of certain materials, and in terms of the specimen being a panel used to evaluate a liquid penetrant. But, it will be appreciated from the following description that the invention may be made from other materials, and that the test piece will be applicable to evaluating other non-destructive inspection techniques used for finding surface flaws. In use, the test piece will be processed in the same way in which an article being inspected is processed.

Figure 1:
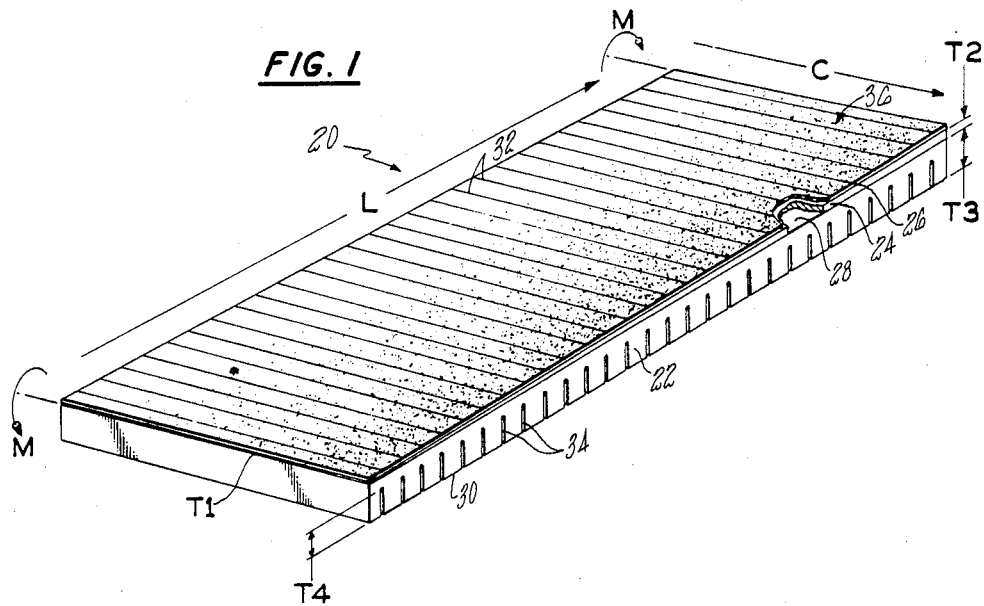
FIG. 1 shows a flat test panel having a multiplicity of spaced apart grooves on one side and a two-layer plating with cracks on the opposing side. The thickness of the plating varies in the direction L while the surface roughness of the plating varies in the direction C.

FIG. 1 shows a tapered test panel 20. The substrate 22 is a rectangular flat piece of brass about 2 mm thick and about 250 mm long by about 40 mm wide. One side 30 has no plating, while the opposing side 28 has on it two platings. First, there is a high residual stress nickel electroplating 24 which varies in thickness along the length L of the panel. The plating has a first thickness T1 at one end, which thickness is nearly zero, and a second greater thickness T2 at the other end, typically of the order of 50 micrometers. Such a plating is called herein a "tapered plating".

Figure 2:
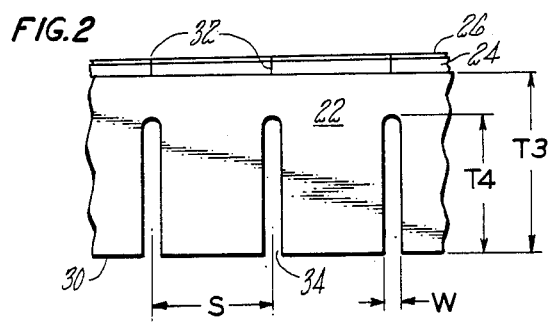
FIG. 2 shows in detail the grooves of the panel of FIG. 1, to illustrate the groove and surface crack relationship.

On top of the nickel tapered plating 24 is a constant thickness chromium plating 26, about 2 micrometers thick. This plating is not an essential part of the invention but is simply placed on the panel in the preferred embodiment in order to provide a hard protective coating for the nickel. The substrate 22 has a multiplicity of slots or grooves 34 running transverse to its length L. These slots extend to a depth T4 which is about 70–80% of the thickness T3 of the substrate, as shown in FIG. 2. The slots or grooves have a relatively small width W of about 0.2–0.5 mm, which dimension is not critical. The pitch S of the grooves is controlled according to where cracks are sought on the plated side of the panel. The desired sensitivity for crack reading will dictate the pitch and number of grooves and cracks. A panel as described here may have about 40 grooves on a pitch of about 6 mm.

Figure 3:
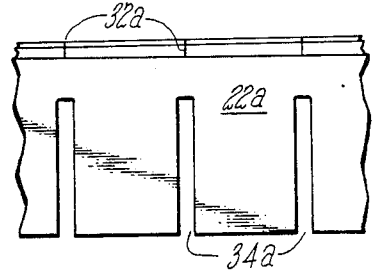
FIGS. 3 and 4 illustrate alternate types of grooves.
Figure 4:
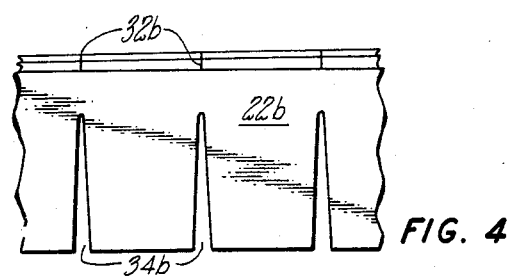

As illustrated by FIGS. 3 and 4 the shape of the slots may be varied. For example, they may have generally rounded bottoms as do the grooves 34 shown in FIGS. 1 and 2; or the rectangular cross section of the grooves 34a; or the sharp apex of the grooves 34b. The grooves may be placed in the substrate by conventional and unconventional machining. Preferably, a disc saw is used. Electric discharge machining, laser beam machining and other procedures can be used. Stress concentrators other than grooves may be used. For example, a series of drilled holes or an embedded dissimilar (low elastic modulus) material in the panel will be substitutional for the grooves.

During its manufacture the panel is first plated as described below. The grooving preferably is done prior to plating but may be done after plating, if desired. Generally, the grooves will be equally spaced along the entire length of the panel but they may optionally be present only in one portion. The next step in the manufacture is to apply to the plate a bending moment as indicated by the arrows M in FIG. 1. This bending moment will produce a tensile stress in the plating as the substrate is bent. Because the plating is located on the outer surface 28 of the substrate, and because when compared to the substrate the nickel plating is both of lower ductility and of substantial higher elastic modulus (about 2.1 GPa vs. 1.25 GPa), the plating will crack. The cracks 32, 32a, 32b will occur preferentially at the locations opposite the grooves 34, 34a, 34b owing to concentration of deflection in the substrate 22, 22a, 22b at such points. The cracks 32 will extend through the plating but will not penetrate the more ductile substrate. (This is an advantage in that a very fine disappearing crack tip is not created, because such a tip tends to accumulate penetrant from one use to the next and thereby distort test results.) Inasmuch as the plating thickness varies along the length, the crack depth and the width as well, will vary. The crack width will typically be 0.16–0.25 of the depth and will be a function of the properties of the plating and substrate.

The plating is preferably applied to the brass subtrate from a nickel sulfamate bath with paramaters chosen to produce high residual stress and apparent brittleness.

The desired plating is called a "high stress plating". The general literature and references cited in the Background give information about suitable plating bath compositions and technique. It is important that the plating be uniform in thickness in the direction transverse to the length of the panel. Thus, undesirable edge effects which are characteristic of electroplating are eliminated either by inserting the panel in a suitable frame, or by trimming the panel after plating to eliminate the undesirable edges. Again, the known references give instruction on this aspect. The tapered plating can be achieved by various techniques, most notably the technique described in the Natori patent application. Other methods of applying varying thickness platings are known as well. It is also within contemplation that a tapered plating thickness characterization can comprise in special situations a series of slight steps rather than a continuous change over the length or a thickness which does not have its lowest point at one extremity. In all instances, the grooving will enable the cracks to occur exactly where desired.

To crack the plating in a tapered test panel, the panel can be bent by various means. The presence of grooves makes the means employed non-critical. For instance, the specimen may be cantilevered from a vise and repeatedly hammered. In doing so, the point of holding is moved progressively to cause the maximum stress concentration to move from groove to groove along the length of the panel. More preferably, the panel is passed through a conventional three roll mill to cause bending. See U.S. Pat. No. 3,279,229 to Lagher. After the panel is bent, the rolls are suitably readjusted and the panel is passed through again to straighten or level it. In its final configuration the panel ought to be as flat as possible, e.g., the curved arc height ought to be less than about 2 mm along the 250 mm length. It is important that the panels be made uniformly flat so that there is reproducibility from one panel to the next. Reproducibility of course will also depend on maintaining consistency in all the other aspects of the panel's manufacture.

Ordinarily, the panel surface 28 will have a uniform mirror finish when its intended function is to comparatively evaluate penetrants. But, as noted above, for more sophisticated use and simulation of particular workpiece conditions, the surface of the panel can be textured. Texturing can be achieved simply by differentially machining or shotblasting the surface 28 of the substrate prior to plating; the finish imparted will be replicated in the plated surface. Machining is preferred because it minimizes any possible residual stress effects on the substrate. Also, the plating parameters may be varied to provide different surface finishes in the plating itself.

And in a particular practice of the invention, the degree of texturing of the panel will vary transversely across the panel in the direction C, as indicated by the variation in finish marks 36 in FIG. 1. Thus, at any given place along the length L where there is a crack, the crack will extend through a gradiation of texture. The capability of a penetrant in finding a particular crack size will thus be measurable according to the variation in surface finish of the panel. A mirror finish panel will have a surface roughness of about 250 micrometer AA (Arithmetic Average) or less while a panel with a texture gradient may vary between the mirror finish and some suitably coarse finish value in the range of 1000 micrometer AA or higher.

While a flat rectangular panel has been described as being the simplest and best mode of the invention, the principles of the invention can also be applied to other shapes of test panels. And while a high residual stress nickel plating is also a well characterized and easily applied surface layer, electroplatings of other materials can be utilized instead, so long as the plating is a dissimilar material which is crack-prone relative to the substrate. Also, surface platings other than electroplating can be used, including such as electroless plates, chemical vapor deposits, and so forth. Of course, the grooves in the substrate which provide the stress concentrations need not be left unfilled after the cracks are formed in the plating. It is possible to fill them with a low melting metal or polymer, or to even machine them away, to provide a smooth surface on the side of the specimen opposite the plating if desired. Other changes in form and detail may be made within the spirit and scope of the invention claimed.

The following is an example of the invention. A flat $250 \times 40$ mm $\times 2$ mm panel is made of AMS 4505F (Aerospace Material Specification of the U.S. Society of Automotive Engineers) annealed brass also known as CDA 26000, having the weight composition 70 Cu 30 Zn. A plating is applied generally according to the general method of AMS 2423. The bath is made essentially of Sulfamate Nickel Plating Solution, available from Allied Kelite Inc., Des Moines, Iowa, USA. To the Solution is added 8.2 g/l (1 oz/gal) chloride (as nickel chloride); 33 g/l (4 oz/gal) boric acid (56% $B_2O_3$), and as required a quantity of Sulfamate Nickel Anti-Pitting Agent from Allied Kelite. The pH is adjusted in the range 3.5–4.5 by adding sulfamic acid or sodium hydroxide. Plating is carried out at a current density of about 0.046–0.092 a/cm$^2$ (0.3–0.6 a/m$^2$). Bath charging and plating parameters are employed which are known to produce in the plating a high residual stress of the order of 170 MPa tension ($\sim 25{,}000$ psi), as measured by a spiral contractometer.

After the desired thickness of tapered nickel plating is applied to the surface, a flash of chromium is applied to the nickel surface using a conventional chromium bath comprised of 250 g/l chromic trioxide ($CrO_3$) and 2.5 g/l concentrated sulfuric acid. Chromium plating is applied using 0.076 amps/cm$^2$ for 15 seconds, followed by 0.18 amps/cm$^2$ for 33 minutes. Reference may also be made to the aforementioned specification MIL-I-8963 (ASG). After inspection, the panel is passed through a three-roll mill wherein it is bent to a radius of curvature of about 175 mm. Then, the rolls are adjusted to a spacing which experiment shows is sufficient to bend the panel to a flat state, when the panel is turned over and passed again through the rolls, as in the prior pass.

Although this invention has been shown and described with respect to a preferred embodiment, it will be understood by those skilled in the art that various changes in form and detail thereof may be made without departing from the spirit and scope of the claimed invention.

We claim:

1. An article for testing the comparative utility of crack penetrants comprised of a substrate having adhered to a first surface a plating of dissimilar material from the substrate, which plating varies in thickness along a length of the substrate, characterized by a plurality of stress concentrators on the second surface of the substrate which opposes the first plated surface, the lengths of the stress concentrators running transverse to the substrate length, the plating having cracks which run essentially parallel to the stress concentrators.

2. The article of claim 1 characterized by stress concentrators in the form of grooves.

3. The article of claim 2 characterized by equally spaced apart grooves having widths of 0.05–0.20 mm.

4. The article of claim 1 characterized by a high stress nickel plating on a comparatively ductile substrate.

5. The article of claim 1 characterized by a substrate which is a flat plate having a plating thickness which tapers between 0–50 micrometers.

6. The article of claim 1 characterized by a first surface which varies in surface texture, from rough to smooth in the direction in which the cracks on the surface run.

7. The method of making an article having a taper thickness plating one side, which article is for testing the comparative utility of surface penetrants, characterized by altering the continuity of the side of the article opposite the plating to concentrate stress at specific locations in the plating when a bending moment is applied to the article, to thereby cause a crack to be associated with each alteration, which crack runs transverse to the direction in which the plating is tapered.

8. The method of claim 7 characterized by altering the article continuity by means of a series of spaced apart grooves which are 70–80% of the article thickness.

* * * * *